United States Patent
Wang et al.

(10) Patent No.: US 9,067,854 B2
(45) Date of Patent: Jun. 30, 2015

(54) DEALKYLATION PROCESS

(71) Applicant: ExxonMobil Chemical Patents Inc., Baytown, TX (US)

(72) Inventors: Kun Wang, Bridgewater, NJ (US); James R. Lattner, LaPorte, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/473,464

(22) Filed: Aug. 29, 2014

(65) Prior Publication Data

US 2014/0371499 A1 Dec. 18, 2014

Related U.S. Application Data

(62) Division of application No. 13/578,755, filed as application No. PCT/US2011/023537 on Feb. 3, 2011, now Pat. No. 8,853,482.

(60) Provisional application No. 61/315,557, filed on Mar. 19, 2010.

(51) Int. Cl.
*C07C 4/18* (2006.01)
*C07C 4/14* (2006.01)
*C07C 5/10* (2006.01)

(52) U.S. Cl.
CPC .............. *C07C 4/18* (2013.01); *C07C 2529/70* (2013.01); *C07C 5/10* (2013.01); *C07C 2521/00* (2013.01); *C07C 2523/00* (2013.01); *C07C 2527/02* (2013.01); *C07C 2527/16* (2013.01); *C07C 2529/06* (2013.01); *C07C 2529/83* (2013.01); *C07C 2529/85* (2013.01)

(58) Field of Classification Search
USPC .................................................. 585/486, 489
See application file for complete search history.

(56) References Cited

U.S. PATENT DOCUMENTS

| | | | |
|---|---|---|---|
| 3,984,490 | A | 10/1976 | Chung et al. |
| 4,152,361 | A | 5/1979 | Imai |
| 4,599,470 | A | 7/1986 | Gregory et al. |
| 4,654,457 | A | 3/1987 | Sato et al. |
| 5,053,571 | A | 10/1991 | Makkee |
| 6,014,018 | A | 1/2000 | Wu et al. |
| 6,037,513 | A | 3/2000 | Chang et al. |
| 6,489,529 | B1 | 12/2002 | Cheng et al. |
| 7,241,930 | B2 | 7/2007 | Schlosberg et al. |
| 7,501,547 | B2 | 3/2009 | Clark et al. |
| 8,633,343 | B2 | 1/2014 | Wang et al. |
| 2008/0242905 | A1 | 10/2008 | Clark et al. |
| 2008/0242907 | A1 | 10/2008 | Clark et al. |

FOREIGN PATENT DOCUMENTS

| | | |
|---|---|---|
| WO | 2006/107462 | 10/2006 |
| WO | 2009/021604 | 2/2009 |
| WO | 2010/138248 | 12/2010 |

OTHER PUBLICATIONS

Farcasiu et al., "*Transalkylation of Polycyclic Aromatics Catalyzed by Trifluoromethanesulfonic Acid*", Energy and Fuels, 1987, vol. 1, pp. 28-31.

*Primary Examiner* — Thuan D Dang
(74) *Attorney, Agent, or Firm* — Siwen Chen; Stephen A. Baehl

(57) ABSTRACT

In a process for dealkylating a poly-alkylated aromatic compound, a feed comprising at least one poly-alkylated aromatic compound selected from polypropylbenzene, polybutylbenzene, and polycyclohexylbenzene is introduced into a reaction zone. The feed is then contacted in the reaction zone with an acid catalyst under conditions effective to dealkylate at least a portion of the poly-alkylated aromatic compound and produce a first reaction product comprising at least one mono-alkylated aromatic compound.

14 Claims, 2 Drawing Sheets

DEALKYLATION PROCESS

PRIORITY CLAIM TO RELATED APPLICATIONS

This application is a divisional of and claims priority to U.S. patent application Ser. No. 13/578,755 filed Aug. 13, 2012, which is a national stage filing of International Patent Cooperation Treaty Application No. PCT/US2011/023537, filed Feb. 3, 2011, which claims priority to U.S. Provisional Application Ser. No. 61/315,557 filed Mar. 19, 2010, both of which are fully incorporated herein by reference in their entirety.

CROSS REFERENCE TO RELATED APPLICATIONS

This application is related to International Patent Cooperation Treaty Application No. PCT/US2010/031029 filed Apr. 14, 2010 and U.S. Pat. No. 6,489,529.

FIELD

The present invention relates to a process for dealkylating poly-alkylated aromatic compounds to produce mono-alkylated aromatic compounds and to the use of the resultant mono-alkylated aromatic compounds in the production of phenol.

BACKGROUND

Polypropylbenzene, polybutylbenzene and polycyclohexylbenzene are significant by-products in the alkylation and hydroalkylation of benzene to produce cumene, butylbenzene, and cyclohexylbenzene respectively. As a result there is significant interest in processes for converting these poly-alkylated aromatic compounds into additional quantities of the desired mono-alkylated aromatic compounds.

Currently, the most common route for the conversion of poly-alkylated aromatic compounds to their monoalkylated counterparts is by transalkylation in which the poly-alkylated species is contacted with an excess of the base aromatic compound in the presence of a transalkylation catalyst. For example, U.S. Pat. No. 6,037,513 discloses that cyclohexylbenzene can be produced by contacting benzene with hydrogen in the presence of a bifunctional hydroalkylation catalyst comprising a molecular sieve of the MCM-22 family and at least one hydrogenation metal selected from palladium, ruthenium, nickel, cobalt, and mixtures thereof. The '513 patent also discloses that any dicyclohexylbenzene in the reaction product can readily be separated from the product stream and converted to additional cyclohexylbenzene by transalkylation with the benzene feed, preferably using the same MCM-22 family molecular sieve as used in the hydroalkylation catalyst but in the absence of the metal components on the hydroalkylation catalyst and in the absence of a hydrogen co-feed.

However, although transalkylation is an effective method of converting poly-alkylated aromatic compounds into their mono-alkylated counterparts, it suffers from the disadvantage that a large excess of base aromatic compound, normally benzene, is required (typically ≥3:1 molar ratio of benzene: heavies), resulting in the need for significant benzene recycle streams. In addition, a low space velocity, and hence a large reactor, is normally required to achieve acceptable conversion in the transalkylation reaction.

According to the present invention, an alternative process for converting poly-alkylated aromatic compounds into additional mono-alkylated product is proposed in which the poly-alkylated aromatic compound is dealkylated, optionally in the presence of hydrogen and/or a small amount of benzene, to produce the mono-alkylated aromatic compound and an alkane or alkene with the same number of carbon atoms as the alkyl groups on the poly-alkylated aromatic compound.

U.S. Pat. No. 3,984,490 discloses a process for recovering phenylcyclohexane as principal product from dicyclohexylbenzenes by heating the latter in the presence of at least an equal amount by weight of benzene and an acid clay or zeolite catalyst at a temperature of 190° C.-400° C. The process in the '490 patent is described as "cracking" but the fact that the conversion requires "at least an equal amount by weight of benzene" suggests that the actual mechanism of the conversion is by transalkylation.

SUMMARY

In one aspect, the invention resides in a process for dealkylating a poly-alkylated aromatic compound, the process comprising:

(a) introducing a feed comprising at least one poly-alkylated aromatic compound selected from polypropylbenzene, polybutylbenzene, and polycyclohexylbenzene into a reaction zone; and (b) contacting the feed in the reaction zone with an acid catalyst under conditions effective to dealkylate at least a portion of the poly-alkylated aromatic compound to produce a first reaction product comprising (i) a first compound comprising a mono-alkylated aromatic compound and (ii) a second compound comprising at least one compound selected from an alkane and alkene with the same number of carbon atoms as an alkyl group on the poly-alkylated aromatic compound.

In one embodiment, the second component comprises at least one compound selected from an alkane and alkene having the same number of carbon atoms as an alkyl group on the poly-alkylated aromatic compound.

In one embodiment, the poly-alkylated aromatic compound is selected from di-isopropylbenzene, tri-isopropylbenzene, and mixtures thereof and the first reaction product comprises (i) cumene and (ii) propylene and/or propane.

In another embodiment, the poly-alkylated aromatic compound is selected from di-sec-butylbenzene, tri-sec-butylbenzene, and mixtures thereof and the first reaction product comprises (i) sec-butylbenzene and (ii) butene and/or butane.

In yet another embodiment, the poly-alkylated aromatic compound is selected from di-cyclohexylbenzene, tri-cyclohexylbenzene, and mixtures thereof and the first reaction product comprises (i) cyclohexylbenzene and (ii) cyclohexene and/or cyclohexane.

Conveniently, the process further comprises introducing benzene into the reaction zone, wherein the weight ratio of benzene to the poly-alkylated aromatic compound in the feed is from 0.01 to about 0.9, such as from about 0.01 to about 0.5.

Conveniently, the process further comprises introducing hydrogen into the reaction zone so that the molar ratio of hydrogen to poly-alkylated aromatic compound in the total feed to the reaction zone is from about 0.01 to about 10.

Conveniently, the acid catalyst is selected from an aluminosilicate, an aluminophosphate, a silicoaluminphosphate, amorphous silica-alumina, an acidic clay, a mixed metal oxide, phosphoric acid, sulfated zirconia, and mixtures thereof. Preferably, the acid catalyst includes at least one aluminosilicate, aluminophosphate or silicoaluminphosphate of the FAU, AEL, AFI and MWW family.

Conveniently, the conditions in (b) include a temperature of about 150° C. to about 500° C. and a pressure of 15 to 500 psig (100 to 3550 kPag).

In one embodiment, the reaction zone is part of a distillation reactor unit.

Conveniently, the process further comprises hydrogenating at least a portion of the first reaction product to produce a second reaction product.

In one embodiment, the process comprises separating the first reaction product into a first fraction comprising the first compound and a second fraction comprising the second compound; and hydrogenating at least a portion of the first fraction to produce the second reaction product.

Conveniently, the hydrogenating is conducted in the presence of a catalyst selected from iron, cobalt, rhodium, palladium, platinum and compounds, and mixtures thereof. Generally, the hydrogenating is conducted at a temperature of about 30° C. to about 200° C. and a pressure of about 200 kPa to about 2000 kPa.

In a further aspect, the invention resides in a process for producing cyclohexylbenzene from benzene, the process comprising:

(a) contacting benzene and hydrogen in a first reaction zone with a catalyst under hydroalkylation conditions to produce a first effluent comprising cyclohexylbenzene, unreacted benzene and at least one polycyclohexylbenzene;

(b) separating at least a portion of the first effluent into a first stream comprising the unreacted benzene, a second stream comprising the cyclohexylbenzene and a third stream comprising the polycyclohexylbenzene;

(c) feeding at least a portion of the third stream and into a second reaction zone; and (d) contacting the feed in the second reaction zone with an acid catalyst under conditions effective to crack at least a portion of the polycyclohexylbenzene and produce a second effluent comprising a first fraction and a second fraction.

In one embodiment, the process further comprises:
(e) feeding the second effluent to the separating step (b).

In one embodiment, the process further comprises:
(f) hydrogenating the at least a portion of the second effluent in a third reaction zone.

In one embodiment, benzene is introduced to the feeding step (c) wherein the weight ratio of benzene to polycyclohexylbenzene in the feed is from 0.01 to about 0.9.

Conveniently, the second and third reaction zones comprise respective parts of a distillation reactor unit.

In one embodiment, the process further comprises:
(g) recycling the first stream produced by the separating step (b) to the contacting step (a).

DETAILED DESCRIPTION OF THE EMBODIMENTS

Figure 1:
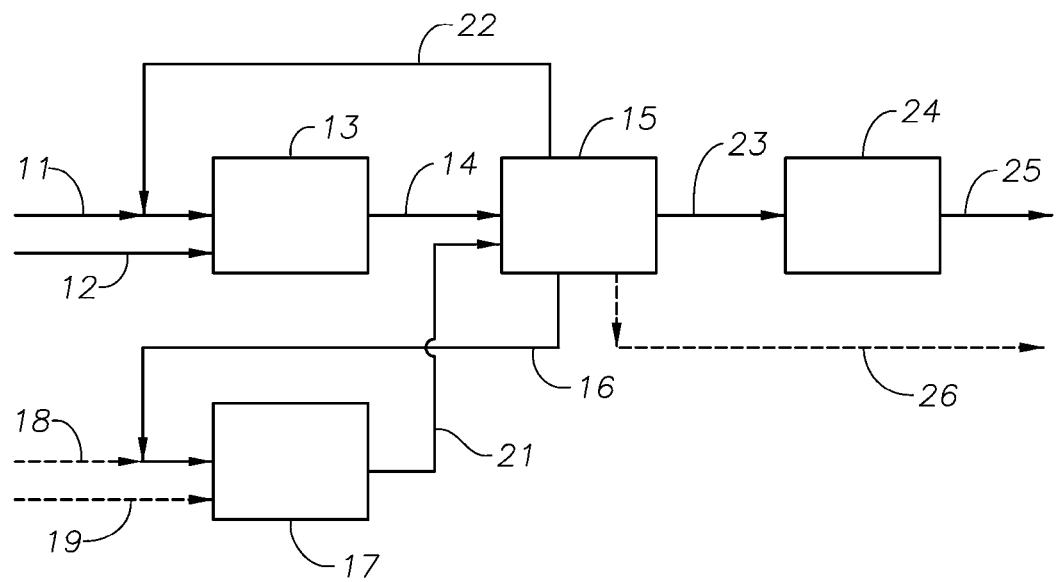
FIG. 1 is a flow diagram of a method for converting benzene to cyclohexylbenzene which includes a dealkylation process according to one example of the invention.

Described herein is a process for dealkylating poly-alkylated aromatic compounds to produce their mono-alkylated derivatives. In particular, there is described a process for dealkylating poly-propylbenzene, poly-butylbenzene, and poly-cyclohexylbenzene produced as by-products in the alkylation or hydroalkylation of benzene to produce cumene, butylbenzene, and cyclohexylbenzene respectively. By way of illustration, the process will now be described in relation to the dealkylation of poly-cyclohexylbenzene produced in the benzene hydroalkylation step of an integrated process for producing phenol from benzene. It will, however, be appreciated that the similar comments apply to the dealkylation of other poly-alkylated aromatic compounds. A "poly-alkylated aromatic compound" is generally defined as aromatic compound having two or more substituents wherein the substituent may be any alkyl or cycloalkyl group having a C number in the range of 2 to 12. An "alkyl group" is generally defined as an alkyl or cycloalkyl substituent. An "alkane" comprises alkanes and cycloalkanes. An "alkene" comprises alkenes and cycloalkenes.

A "poly-alkylated aromatic compound" is generally defined as having two or more substituents on an aromatic compound wherein the substituent may be any alkyl, aryl, or alicyclic group.

Benzene Hydroalkylation

Benzene hydroalkylation is a two stage process involving the initial reaction of one molecule of benzene with hydrogen to form cyclohexene which then alkylates a further benzene molecule to produce cyclohexylbenzene (CHB). The overall reaction is summarized at (1) below:

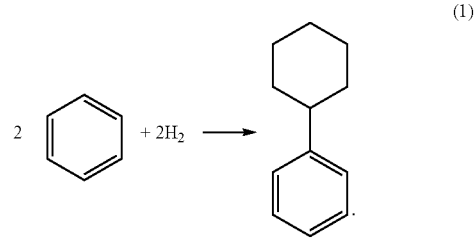 [SMILES: c1ccccc1 ; c1ccc(C2CCCCC2)cc1]

Competing reactions include the complete saturation of the benzene to produce cyclohexane, polyalkylation to produce mainly dicyclohexylbenzene, and reorganization/alkylation reactions to produce other impurities, such as methylcyclopentylbenzene. Since polyalkylation is generally the most significant side-reaction, the present process focuses on the removal of poly-cyclohexylbenzenes by dealkylation or cracking to produce additional mono-cyclohexylbenzene.

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The hydroalkylation reaction employs a bifunctional catalyst, which typically comprises a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst, and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia and silica-magnesia-zirconia.

Dealkylation of Poly-Cyclohexylbenzene

Although the hydroalkylation step is highly selective towards cyclohexylbenzene, the effluent from the hydroalkylation reaction normally contains of the order of 20 wt % of poly-cyclohexylbenzenes, as well as unreacted aromatic feed and the desired monoalkylated species. The unreacted aromatic feed is recovered for recycle to the alkylation reactor by passing the hydroalkylation reaction effluent to a first distillation tower. The bottoms from the first distillation tower are then fed to a second distillation tower to separate the mono-cyclohexylbenzene product from any poly-cyclohexylbenzenes and other heavies. The poly-cyclohexylbenzenes are then dealkylated to produce additional monocyclohexylbenzene product.

Dealkylation is typically effected in a reactor separate from the hydroalkylation reactor, such as a reactive distillation unit, over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Generally, the acid catalyst includes at least one aluminosilicate, aluminophosphate or silicoaluminphosphate of the FAU, AEL, AFI and MWW family.

Unlike transalkylation, which generally is conducted in a molar excess of additional benzene, the present dealkylation process can be conducted in the absence of added benzene. In some cases, however, it may be desirable to add benzene to the dealkylation reaction to reduce coke formation, in which case the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

The conditions employed in the dealkylation reaction are not narrowly confined but generally include a temperature of about 150° C. to about 500° C. and a pressure of 15 to 500 psig (100 to 3550 kPag).

The main reaction occurring in the present dealkylation process is summarized at (2) below:

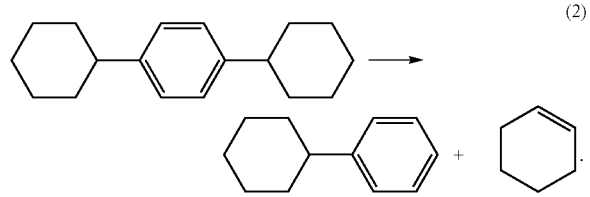

(2)

Thus, in addition to monocyclohexylbenzene, the product of the dealkylation reaction contains cyclohexene and/or, if hydrogen is present, cyclohexane normally together with unreacted poly-cyclohexylbenzenes. The dealkylation reaction product is therefore fed to a distillation unit, normally the first and second distillation towers used to fractionate the hydroalkylation effluent. In the distillation unit, the cyclohexene and/or cyclohexane are initially removed from the dealkylation product and recycled to the hydroalkylation unit with the unreacted benzene from the hydroalkylation effluent. In the hydroalkylation unit, the recycled cyclohexene will react with benzene forming cyclohexylbenzene and/or polycyclohexylbenzenes.

The unreacted poly-cyclohexylbenzenes in the dealkylation reaction product are then separated from the remainder of the dealkylation product for recycle to the dealkylation process, leaving a $C_{12}$ fraction containing the desired cyclohexylbenzene product.

The $C_{12}$ fraction is then normally subjected to a hydrogenation step to remove possible trace amounts of olefins, such as phenylcyclohexene, before the cyclohexylbenzene product is recovered for conversion to phenol. Hydrogenation is conveniently effected by contacting the $C_{12}$ fraction with a supported metal catalyst at a temperature of about 30° C. to about 200° C., a pressure of about 200 kPa to about 2000 kPa and a molar ratio of hydrogen to hydrocarbon feed of about 0.01 to about 100. Suitable metal catalysts include iron, cobalt, rhodium, palladium, platinum and compounds, and mixtures thereof and suitable supports include alumina, silica, carbon, zirconia, titania and mixtures thereof.

Phenol Production

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide. Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 mol % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Following the oxidation step, the cyclohexylbenzene hydroperoxide is converted via a cleavage reaction into phenol and cyclohexanone. Cleavage is conveniently effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol, or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid, and p-toluenesulfonic acid. Ferric chloride, boron trifluoride, sulfur dioxide, and sulfur trioxide are also effective homogeneous cleavage catalysts. The preferred homogeneous cleavage catalyst is sulfuric acid, with preferred concentrations in the range of about 0.05 to about 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

The invention will now be more particularly described with reference to the accompanying drawings.

Referring to FIG. 1, this is a flow diagram of the hydroalkylation and dealkylation stages of an integrated process according to one example of the invention for converting benzene to phenol. In the process shown in FIG. 1, fresh benzene (line 11) and hydrogen (line 12) are introduced to a hydroalkylation reactor 13, where the benzene undergoes hydroalkylation to produce cyclohexylbenzene (CHB) and poly-cyclohexylbenzenes (PCHB). The effluent from the reactor 13, containing unreacted benzene in addition to the CHB and PCHB, is removed via line 14 and fed to a distillation system 15, which divides the effluent into a $C_6$ fraction, a $C_{12}$ fraction and a $C_{18}$ fraction.

The $C_{18}$ fraction from the distillation system 15 is rich in the PCHB by-product from the hydroalkylation reaction and is fed by line 16 to a cracking reactor 17, which optionally also receives benzene from line 18 and hydrogen from line 19. The PCHB by-product is dealkylated in the cracking reactor 17 to produce additional monocyclohexylbenzene product, together with cyclohexene and/or cyclohexane. The effluent from the cracking reactor 17 is then fed via line 21 back to the distillation system 15, where the additional monocyclohexylbenzene product is separated as part of the $C_{12}$ fraction while the cyclohexene and/or cyclohexane are removed as part of the $C_6$ fraction. Any unreacted PCHB in the effluent from the cracking reactor is removed as part of the $C_{18}$ fraction and recycled to the dealkylation step. If desired part of the heavies, such as the $C_{18}$ fraction, from the distillation system 15 can be purged via line 26 to avoid the build-up of unwanted by-products in the recycle loop 16, 21.

The $C_6$ fraction from the distillation system 15 contains unreacted benzene, cyclohexene, and/or cyclohexane and is recycled via line 22 to the hydroalkylation reactor 13.

The $C_{12}$ fraction from the distillation system 15 contains monocyclohexylbenzene product from both the hydroalkylation reactor 13 and the cracking reactor 17 and is fed via line 23 to a hydrogenation reactor 24 before being supplied via line 25 to the oxidation and cleavage sections (not shown) of the phenol process.

Figure 2:
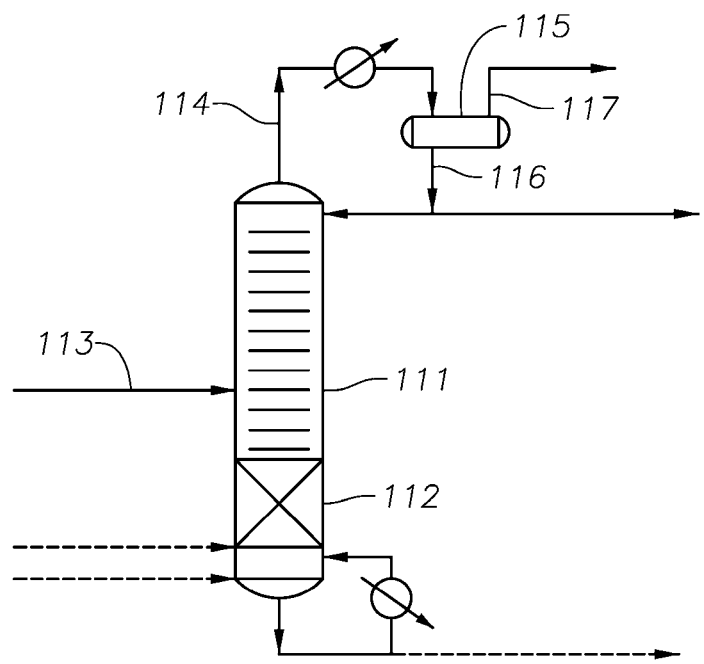
FIG. 2 is a diagram of a first reactive distillation unit for performing the dealkylation process according to the one example of the invention.

FIG. 2 is a diagram of a reactive distillation unit for conducting the dealkylation step of the process shown in FIG. 1. The embodiment shown in FIG. 2 includes a vertical distillation tower 111 which is provided with a cracking zone 112 located near the base of the tower, which also receives the optional benzene and hydrogen feeds. The product of the hydroalkylation reactor, after removal of the unreacted benzene, is introduced by line 113 into the tower mid-way along the tower 111. On entering the distillation tower 111, the hydroalkylation product is separated into a $C_{18}$ fraction, which descends through the tower to the cracking zone 112, and a $C_{12}$ fraction which leaves the tower as overhead 114. The $C_{18}$ fraction is dealkylated in the cracking zone to produce monocyclohexylbenzene product cyclohexene, and/or cyclohexane, which exit the tower 111 as part of the overhead 114. The overhead is then passed through a cooler 115 to remove any unreacted PCHB, which is recycled to the tower via line 116 and any unreacted hydrogen, which is vented from the cooler via line 117. The remaining overhead, which is composed mainly of cyclohexylbenzene, cyclohexene, and/or cyclohexane, is then passed to a distillation system (not shown) to separate the $C_6$ and $C_{12}$ fractions. Any unreacted $C_{18}$ and heavier compounds (i.e., heavies) exit through the bottoms stream of the column.

Figure 3:
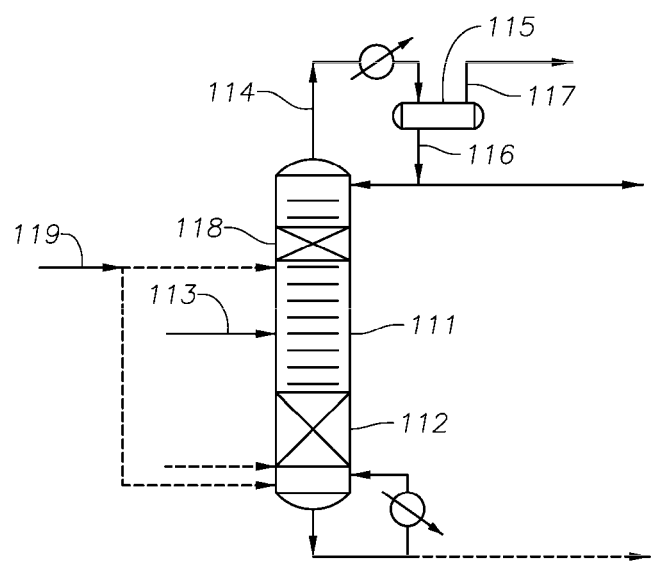
FIG. 3 is a diagram of a second reactive distillation unit for performing the dealkylation process according to the one example of the invention together with hydrogenation of the cyclohexylbenzene-containing $C_{12}$ stream.

FIG. 3 is a diagram of an alternative reactive distillation unit for conducting both the dealkylation and hydrogenation steps of the process shown in FIG. 1. The unit shown in FIG. 3 is similar to that used in the process of FIG. 2 and so like reference numerals are used to illustrate the same components in FIGS. 2 and 3. The unit shown in FIG. 3 again includes a vertical distillation tower 111 which is provided with a cracking zone 112 near the base of the tower but which also includes a hydrogenation zone 118 near the top of the tower. Hydrogen is introduced through line 119 into the tower 111 directly beneath the hydrogenation zone 118 and further hydrogen and/or benzene may be introduced near the base of the tower. Any unreacted $C_{18}$ and heavier compounds (i.e. heavies) exit through the bottoms stream of the column.

As in the case of FIG. 2, the product of the hydroalkylation reactor, after removal of the unreacted benzene, is introduced by line 113 into the tower mid-way along the tower 111, where the hydroalkylation product is separated into a $C_{18}$ fraction and a $C_{12}$ fraction. As before, the $C_{18}$ fraction descends through the tower to the cracking zone 112, where the $C_{18}$ fraction is dealkylated to produce monocyclohexylbenzene product, cyclohexene and/or cyclohexane. The dealkylated product then passes back up through the tower and combines with the $C_{12}$ fraction of the hydroalkylation product before exiting the tower 111 as overhead 114. The overhead is then passed through a cooler 115 to remove any unreacted PCHB, which is recycled to the tower via line 116 and any unreacted hydrogen, which is vented from the cooler via line 117. The remaining overhead, which is composed mainly of cyclohexylbenzene, cyclohexene and/or cyclohexane, is then passed to a distillation system (not shown) to separate the $C_6$ and $C_{12}$ fractions.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

Additionally or alternately, the invention can be described by the following embodiments:

1. A process for dealkylating a poly-alkylated aromatic compound, the process comprising:
   (a) introducing a feed comprising at least one poly-alkylated aromatic compound selected from polypropylbenzene, polybutylbenzene, and polycyclohexylbenzene into a reaction zone; and
   (b) contacting the feed in the reaction zone with an acid catalyst under conditions effective to dealkylate at least a portion of the poly-alkylated aromatic compound to produce a first reaction product comprising (i) a first compound comprising at least one mono-alkylated aromatic compound and (ii) a second compound comprising at least one compound selected from an alkane and alkene.

2. The process of embodiment 1, wherein the poly-alkylated aromatic compound is selected from di-isopropylbenzene, tri-isopropylbenzene, and mixtures thereof and the first reaction product comprises (i) cumene and (ii) propylene and/or propane.

3. The process of embodiment 1, wherein the poly-alkylated aromatic compound is selected from di-sec-butylbenzene, tri-sec-butylbenzene, and mixtures thereof and the first reaction product comprises (i) sec-butylbenzene and (ii) butene and/or butane.

4. The process of embodiment 1, wherein the poly-alkylated aromatic compound is selected from di-cyclohexylbenzene, tri-cyclohexylbenzene, and mixtures thereof and the first reaction product comprises (i) cyclohexylbenzene and (ii) cyclohexene and/or cyclohexane.

5. The process of embodiment 1, and further comprising the step of introducing benzene into the reaction zone, wherein the weight ratio of benzene to the poly-alkylated aromatic compound in the feed is from 0.01 to about 0.9.

6. The process of embodiment 5, wherein the weight ratio of benzene to the poly-alkylated aromatic compound in the feed is from 0.01 to about 0.5.

7. The process of embodiment 1, and further comprising the step of introducing hydrogen into the reaction zone so that the molar ratio of hydrogen to poly-alkylated aromatic compound in the total feed to the reaction zone is from about 0.01 to about 10.

8. The process of embodiment 1, wherein the acid catalyst is selected from an aluminosilicate, an aluminophosphate, a silicoaluminphosphate, amorphous silica-alumina, an acidic clay, a mixed metal oxide, phosphoric acid, sulfated zirconia, and mixtures thereof.

9. The process of embodiment 1, wherein the acid catalyst is selected from an aluminosilicate, aluminophosphate, or silicoaluminphosphate of the FAU, AEL, AFI and MWW family.

10. The process of embodiment 1, wherein the conditions include a temperature of about 150° C. to about 500° C. and a pressure of 15 to 500 psig (100 to 3550 kPag).

11. The process of embodiment 1, wherein the reaction zone is part of a distillation reactor unit.

12. The process of embodiment 1 and further comprising hydrogenating at least a portion of the first reaction product.

13. The process of embodiment 1 and further comprising:
(c) separating the first reaction product into a first fraction comprising the first compound and a second fraction comprising the second compound; and
(d) hydrogenating at least a portion of the first fraction to produce a second reaction product.

14. The process of embodiment 13, wherein the hydrogenating is conducted at a temperature of about 30° C. to about 200° C. and a pressure of about 200 kPa to about 2000 kPa.

15. A process for producing cyclohexylbenzene from benzene, the process comprising:
(a) contacting benzene and hydrogen in a first reaction zone with a catalyst under hydroalkylation conditions to produce a first effluent comprising cyclohexylbenzene, unreacted benzene, and at least one polycyclohexylbenzene;
(b) separating at least a portion of the first effluent into a first stream comprising the unreacted benzene, a second stream comprising the cyclohexylbenzene and a third stream comprising the polycyclohexylbenzene;
(c) feeding at least a portion of the third stream into a second reaction zone; and
(d) contacting the third stream in the second reaction zone with an acid catalyst under conditions effective to dealkylate at least a portion of the polycyclohexylbenzene and produce a second effluent comprising at least one $C_6$ compound and at least one $C_{12}$ compound.

16. The process of embodiment 15, further comprising
(e) feeding at least a portion of the second effluent to the separating step (b).

17. The process of embodiment 15, further comprising feeding benzene into a second reaction zone wherein the weight ratio of benzene to polycyclohexylbenzene in the feed is from 0.01 to about 0.9.

18. The process of embodiment 15, wherein the acid catalyst is selected from an aluminosilicate, an aluminophosphate, a silicoaluminphosphate, amorphous silica-alumina, an acidic clay, a mixed metal oxide, phosphoric acid, sulfated zirconia, and mixtures thereof 19. The process of embodiment 15 wherein the acid catalyst includes at least one aluminosilicate, aluminophosphate, or silicoaluminphosphate of the FAU, AEL, AFI and MWW families.

20. The process of embodiment 15, wherein the weight ratio of benzene to polycyclohexylbenzene in the feed is from 0 to about 0.5.

21. The process of embodiment 15, wherein hydrogen is also introduced into the reaction zone in (a) so that the molar ratio of hydrogen to polycyclohexylbenzene in the total feed to the reaction zone is from about 0.01 to about 10.

22. The process of embodiment 15, wherein the conditions in the contacting step (d) include a temperature of about 150° C. to about 500° C. and a pressure of 15 to 500 psig (100 to 3550 kPag).

23. The process of embodiment 15, wherein the first and second reaction zones comprise respective parts of a distillation reactor unit.

24. The process of embodiment 15 and further comprising:
(f) hydrogenating at least a portion of the second effluent in a third reaction zone.

25. The process of embodiment 22, wherein the first, second and third reaction zones comprise respective parts of a distillation reactor unit.

The invention claimed is:

1. A process for dealkylating a poly-alkylated aromatic compound, the process comprising:
(a) introducing a feed comprising at least one poly-alkylated aromatic compound selected from polypropylbenzene, polybutylbenzene, and polycyclohexylbenzene into a reaction zone; and
(b) contacting the feed in the reaction zone with an acid catalyst under conditions effective to dealkylate at least a portion of the poly-alkylated aromatic compound to produce a first reaction product comprising (i) a first compound comprising at least one mono-alkylated aromatic compound and (ii) a second compound comprising at least one compound selected from an alkane and alkene.

2. The process of claim 1, wherein the poly-alkylated aromatic compound is selected from di-isopropylbenzene, tri-isopropylbenzene, and mixtures thereof and the first reaction product comprises (i) cumene and (ii) propylene and/or propane.

3. The process of claim 1, wherein the poly-alkylated aromatic compound is selected from di-sec-butylbenzene, tri-sec-butylbenzene, and mixtures thereof and the first reaction product comprises (i) sec-butylbenzene and (ii) butene and/or butane.

4. The process of claim 1, wherein the poly-alkylated aromatic compound is selected from di-cyclohexylbenzene, tri-cyclohexylbenzene, and mixtures thereof and the first reaction product comprises (i) cyclohexylbenzene and (ii) cyclohexene and/or cyclohexane.

5. The process of claim 1, and further comprising the step of introducing benzene into the reaction zone, wherein the weight ratio of benzene to the poly-alkylated aromatic compound in the feed is from 0.01 to about 0.9.

6. The process of claim 1, wherein the weight ratio of benzene to the poly-alkylated aromatic compound in the feed is from about 0.01 to about 0.5.

7. The process of claim 1, and further comprising the step of introducing hydrogen into the reaction zone so that the molar ratio of hydrogen to poly-alkylated aromatic compound in the total feed to the reaction zone is from about 0.01 to about 10.

8. The process of claim 1, wherein the acid catalyst is selected from an aluminosilicate, an aluminophosphate, a silicoaluminphosphate, amorphous silica-alumina, an acidic clay, a mixed metal oxide, phosphoric acid, sulfated zirconia, and mixtures thereof.

9. The process of claim 1, wherein the acid catalyst is selected from at least one aluminosilicate, aluminophosphate, or silicoaluminphosphate of the FAU, AEL, AFI and MWW family.

10. The process of claim 1, wherein the conditions include a temperature of about 150° C. to about 500° C. and a pressure of 15 to 500 psig (100 to 3550 kPag).

11. The process of claim 1, wherein the reaction zone is part of a distillation reactor unit.

12. The process of claim 1, and further comprising hydrogenating at least a portion of the first reaction product.

13. The process of claim 1, and further comprising:
(c) separating the first reaction product into a first fraction comprising the first compound and a second fraction comprising the second compound; and
(d) hydrogenating at least a portion of the first fraction to produce a second reaction product.

14. The process of claim 13, wherein the hydrogenating step (d) is conducted at a temperature of about 30° C. to about 200° C. and a pressure of about 200 kPa to about 2000 kPa.

* * * * *